United States Patent
Ozer

(10) Patent No.: US 9,067,904 B2
(45) Date of Patent: *Jun. 30, 2015

(54) VAPOR-PHASE DECARBONYLATION PROCESS

(75) Inventor: Ronnie Ozer, Arden, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 1039 days.

This patent is subject to a terminal disclaimer.

(21) Appl. No.: 13/122,740

(22) PCT Filed: Dec. 8, 2009

(86) PCT No.: PCT/US2009/067092
§ 371 (c)(1),
(2), (4) Date: Apr. 6, 2011

(87) PCT Pub. No.: WO2010/071745
PCT Pub. Date: Jun. 24, 2010

(65) Prior Publication Data
US 2011/0196126 A1     Aug. 11, 2011

Related U.S. Application Data

(60) Provisional application No. 61/138,754, filed on Dec. 18, 2008.

(51) Int. Cl.
*C08G 65/20* (2006.01)
*C07D 307/36* (2006.01)

(52) U.S. Cl.
CPC .................................. *C07D 307/36* (2013.01)

(58) Field of Classification Search
CPC ..................................................... C07D 307/36
USPC .................................. 549/505, 506; 528/417
See application file for complete search history.

(56) References Cited

U.S. PATENT DOCUMENTS

| | | | |
|---|---|---|---|
| 2,634,276 A * | 4/1953 | Carnahan | 549/505 |
| 3,007,941 A | 11/1961 | Copelin | |
| 3,223,714 A | 12/1965 | Manly | |
| 3,257,417 A * | 6/1966 | Dunlop et al. | 549/505 |
| 4,780,552 A | 10/1988 | Wambach | |
| 2008/0216391 A1 | 9/2008 | Cortright | |

FOREIGN PATENT DOCUMENTS

| | | |
|---|---|---|
| CN | 101422738 | 5/2009 |
| EP | 96913 B1 | 10/1986 |
| JP | 2009132656 A | 6/2009 |

OTHER PUBLICATIONS

Coca, J., Catalytic Decarbonylation of Furfural in a Fixed-Bed Reactor, 1982, J. Chem. Tech. Biotechnol., 32, 904-908.*
Lejemble et al, From Biomass to Furan Through Decarbonylation of Furfural Under Mild Conditions, Biomass, 4 (1984), 263-274.
U.S. Appl. No. 13/124,574, filed Apr. 15, 2011 to Li, Ke et al.

* cited by examiner

*Primary Examiner* — Noble Jarrell
*Assistant Examiner* — John Mauro

(57) ABSTRACT

A process is provided for the synthesis of furan and related compounds by vapor phase decarbonylation of furfural and derivatives. The reaction rate, conversion, and selectivity are enhanced by adding water to the feed. The process can be run at lower temperatures than in similar processes run with essentially dry furan and related compounds.

14 Claims, No Drawings

VAPOR-PHASE DECARBONYLATION PROCESS

CROSS-REFERENCE TO RELATED APPLICATIONS

This application claims the benefit of U.S. Provisional Application No. 61/138,754, filed Dec. 18, 2008, which is incorporated in its entirety as a part hereof for all purposes.

FIELD OF DISCLOSURE

The disclosure relates to the manufacture of furan and related compounds, and to the industrial use thereof for the synthesis of other useful materials.

BACKGROUND

Furan and related compounds are useful starting materials for industrial chemicals for use as pharmaceuticals, herbicides, stabilizers, and polymers. For example, furan is used to make tetrahydrofuran, polytetramethylene glycol, polyetherester elastomers, and polyurethane elastomers.

Known transition metal catalyzed, vapor phase processes to produce furan by decarbonylation of furfural are limited by either the selectivity or lifetime of the supported catalyst. The conversion of furfural to furan is complicated by the tendency to form polymeric or carbonizing byproducts which foul the catalyst surface and hinder the rate and lifetime of the catalyst. For example, U.S. Pat. No. 3,223,714 teaches a continuous low pressure vapor phase decarbonylation process for the production of furan comprising contacting furfural vapor with a supported palladium catalyst. A preferred catalyst has about 0.3 wt % Pd supported on alumina. The catalyst can be regenerated in situ but the lifetime of a running cycle for the catalyst is short and the production of furan per cycle is low.

There remains a need for a vapor phase process for the decarbonylation of furfural to furan with improved rates.

DESCRIPTION

The inventions disclosed herein include processes for the preparation of furan and for the preparation of products into which furan can be converted.

Features of certain of the processes of this invention are described herein in the context of one or more specific embodiments that combine various such features together. The scope of the invention is not, however, limited by the description of only certain features within any specific embodiment, and the invention also includes (1) a subcombination of fewer than all of the features of any described embodiment, which subcombination can be characterized by the absence of the features omitted to form the subcombination; (2) each of the features, individually, included within the combination of any described embodiment; and (3) other combinations of features formed by grouping only selected features taken from two or more described embodiments, optionally together with other features as disclosed elsewhere herein. Some of the specific embodiments of the processes hereof are as follows:

In one embodiment hereof, this invention provides a process for the synthesis of a compound as represented by the following structure of Formula (I)

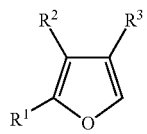

by (a) providing a vapor phase mixture of water and a compound as represented by the following structure of Formula (II),

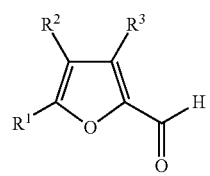

wherein the water is present at about 1 to about 30 wt % based on the weight of water plus Formula (II) compound; (b) optionally co-feeding the Formula (II) compound with hydrogen, (c) heating a supported Pd catalyst, and (d) contacting the vapor phase mixture and the catalyst to produce a Formula (I) product; wherein $R^1$, $R^2$, and $R^3$ are each independently selected from H and a $C_1$ to $C_4$ hydrocarbyl group.

In another embodiment hereof, a process is provided for preparing a Formula (I) product, as described above, that further includes a step of subjecting the furan to a reaction (including a multi-step reaction) to prepare therefrom a compound (such as that useful as a monomer), oligomer or polymer.

Advantageous features of the processes hereof include higher rates of decarbonylation, higher conversion of Formula (II) compounds, and higher selectivity for Formula (I) product, while running at lower temperature than in similar processes run with essentially dry Formula (II) compounds.

In one embodiment of the processes described herein, $R^1$, $R^2$, and $R^3$ all equal H; thus, the Formula (I) product is furan and the Formula (II) compound is furfural. The decarbonylation of furfural to produce furan can then be represented by the following equation:

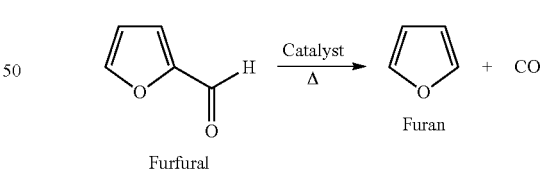

The Formula (II) compound used in the processes described herein is preferably obtained from a biological material which is a good source of hemicellulose. Examples include without limitation: straw, corn cobs, corn stalks (stover), sugar bagasse, hardwoods, cotton stalks, kenaf, oat hulls, and hemp. The Formula (II) compound, especially when it is furfural, should be freshly distilled before use, since it can oxidize and change color, producing undesirable high-boiling oxidation products.

In the processes described herein, the decarbonylation reaction is catalyzed by a supported Pd catalyst. In one embodiment, the Pd is supported on alumina. The amount of Pd is not critical; in one embodiment, it is present at 0.1 to 2 wt % (based on Pd+alumina, or total catalyst weight).

The reaction is conducted by injecting a vapor phase mixture of water and Formula (II) compound into a reactor that is loaded with the desired catalyst. As used herein, the term "vapor phase mixture" means that the components of the mixture are gases. The water can be added to the Formula (II) compound either as a liquid to the liquid Formula (II) compound before volatilization or as a gas to gaseous Formula (II) compound.

Where liquid water is added to liquid Formula (II) compound to form a mixture, the mixture is heated to a temperature high enough to vaporize the mixture; when the Formula (II) compound is furfural and water is present at about 3 wt %, this is about 180° C. A non-reactive internal standard (e.g., dodecane) can be present in the Formula (II) compound at about 0.5 wt % for analytical purposes, i.e., to confirm mass balance.

In an embodiment, hydrogen is co-fed to help volatilize the Formula (II) compound; hydrogen is also known to extend catalyst life. The hydrogen to Formula (II) molar ratio is typically between 0.1 and 5.0.

The reaction can occur in the vapor (i.e., gas) phase at a temperature that can suitably be in the range of from about 200° C. to about 400° C., generally in the range of from about 270° C. to about 330° C. The reaction temperature referred to here is the temperature that has been provided for the catalyst in the catalyst zone of the reactor. A temperature in these ranges is provided by heating the various portions of the reactor from a source external thereto, in particular a heating element designed to surround and heat the catalyst zone of the reactor, and thus the catalyst itself. The selected temperature thus exists in the catalyst zone of the reactor upon the occasion when the furfural is contacted with the catalyst.

The reaction is generally run at ambient pressure or slightly above. The pressure is not critical, as long as the Formula (I) and Formula (II) compounds remain in the gas phase in the reactor. The reaction residence time can be a minute or less, or about 5 to about 10 seconds, or about 1 to about 2 seconds, or less than one second. The reaction is run with continuously fed Formula (I) compound and, preferably, hydrogen for a length of time suitable to determine the lifetime of the catalyst. For example, a lifetime is calculated as the grams of furan produced per gram of Pd in the reactor. A lifetime of greater than 10,000 grams per gram Pd is desirable, greater than 100,000 grams per g Pd more so. In all cases, however, the reaction is carried out at a temperature and pressure and for a time that is sufficient to obtain gas-phase production of the Formula (I) compound. Supported Pd catalyst is known to degrade in activity over time through a number of mechanisms: 1) fouling, that is, the coating of the active sites with carbon ("carbonization"), 2) poisoning, that is, the disabling of active sites through reaction with process impurities, and 3) sintering, that is, the migration of Pd on the surface of the catalyst to produce a larger average Pd crystallite size and hence less available Pd surface for the reaction. The deactivation via pathway 1, carbonization, can be reversed through burning the carbon off the catalyst surface using an oxygen-containing gas stream. However, Pd catalysts are known to be susceptible to deactivation via pathway 3, sintering, at temperatures normally associated with oxidative regeneration. The catalyst can instead be regenerated in a dilute oxygen stream with an excess of steam to draw the heat produced by the oxidative exotherm rapidly away from the catalyst surface. Dilution with nitrogen is also possible, though less preferable owing to its lack of heat capacity for cooling the catalyst bed. The regeneration can be done by feeding air, or a mixture of air with steam or nitrogen, to the catalyst bed at a temperature range of between about 300° C. and about 500° C. for a time between about 10 seconds and about 100 hours. The concentration of air in the mixture of air with steam or nitrogen is at least 0.1 vol %, at least 1 vol %, at least 5 vol %, at least 10 vol %, at least 20 vol %, at least 30 vol %, at least 40 vol %, at least 50 vol %, at least 60 vol %, at least 70 vol %, at least 80 vol %, at least 90 vol %, at least 95 vol %, or at least 99 vol %.

Reactors suitable for use in the processes hereof include fixed-bed reactors and pipe, tubular or other plug-flow reactors and the like in which the catalyst particles are held in place and do not move with respect to a fixed residence frame; and fluidized bed reactors. Reactants can be flowed into and through reactors such as these on a continuous basis to give a corresponding continuous flow of product at the downstream end of the reactor. These and other suitable reactors are more particularly described, for example, in Fogler, *Elements of Chemical Reaction Engineering*, 2nd Edition, Prentice-Hall Inc. (1992). In one embodiment, in-flow lines are heat traced to keep the reactant at a suitable temperature, and the temperature of the catalyst zone is controlled by a separate heating element at that location. The Formula (I) product, as obtained from the reactor in the form of a gas, can be condensed by cooling to a liquid for ease of further handling. Alternatively, the process can further comprise purifying the Formula (I) product, such as by distillation. For example, the Formula (I) product can be fed directly into, e.g., a distillation column to remove unreacted Formula (II) compound and other impurities that may be present; the distilled product can then be isolated and recovered.

The distilled product can also, however, be subjected with or without recovery from the reaction mixture to further steps to convert it to another product such as another compound (such as a type useful, for example, as a monomer), or an oligomer or a polymer. Another embodiment of a process hereof thus provides a process for converting the Formula (I) product, through a reaction (including a multi-step reaction), into another compound, or into an oligomer or a polymer. For example, the Formula (I) product furan can be made from the Formula (II) compound furfural by a process such as described above, and then converted into tetrahydrofuran by hydrogenation. The tetrahydrofuran can in turn be used for preparation of polytetramethylene ether glycol, which in turn can be reacted with 1,4-butanediol and terephthalic acid to produce polyetherester elastomers, or with diisocyanates to produce polyurethanes.

All publications, patent applications, patents, and other references mentioned herein are incorporated by reference in their entirety. Unless otherwise defined, all technical and scientific terms used herein have the same meaning as commonly understood by one of ordinary skill in the art to which this invention belongs. In case of conflict, the present specification, including definitions, will control.

Although methods and materials similar or equivalent to those described herein can be used in the practice or testing of the present invention, suitable methods and materials are described herein.

Unless stated otherwise, all percentages, parts, ratios, etc., are by weight.

When an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

When the term "about" is used in describing a value or an end-point of a range, the disclosure should be understood to include the specific value or end-point referred to.

As used herein, the terms "comprises," "comprising," "includes," "including," "containing," "characterized by," "has," "having" or any other variation thereof, are intended to cover a non-exclusive inclusion. For example, a process, method, article, or apparatus that comprises a list of elements is not necessarily limited to only those elements but can include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Use of "a" or "an" are employed to describe elements and components of the invention. This is done merely for convenience and to give a general sense of the invention. This description should be read to include one or at least one and the singular also includes the plural unless it is obvious that it is meant otherwise.

The materials, methods, and examples herein are illustrative only and, except as specifically stated, are not intended to be limiting.

EXAMPLES

The advantageous attributes and effects of the processes hereof can be seen in a series of examples (Examples 1~2), as described below. The embodiments of these processes on which the examples are based are representative only, and the selection of those embodiments to illustrate the invention does not indicate that conditions, arrangements, approaches, regimes, steps, techniques, configurations, protocols or reactants not described in these examples are not suitable for practicing these processes, or that subject matter not described in these examples is excluded from the scope of the appended claims and equivalents thereof.
Materials.

The following materials were used in the examples.

Furfural was obtained from HHI, China, having a pre-distillation purity 98.5%. It was used freshly distilled (20 plate 1 inch (2.54 cm) Oldershaw column batchwise) prior to a run with minimal air contact.

Pd/α-alumina catalyst (0.1% Pd) was obtained from Johnson Matthey PLC, London, England.

Deionized water was used.

The meaning of abbreviations is as follows: "cm" means centimeter(s), "conv" means conversion, "g" means gram(s), "GC/MS" means gas chromatography/mass spectroscopy, "h" means hour(s), "mL" means milliliter(s), "min" means minutes, "sel" means selectivity, "temp" means temperature, and "wt %" means weight percent(age).

Example 1

Run 1A. A mixture of distilled furfural containing 3 wt % added water was prepared. The liquid was fed to a ½" (1.27 cm) tubular downflow reactor at 290° C. at a liquid feed rate of 1 mL/h to a 2 gram catalyst bed made of 0.1% Pd on α-alumina support. Hydrogen was co-fed at a rate of 8.5 cm$^3$/min to help prevent deactivation of the Pd catalyst Run 1 B. Run 1A was repeated without added water and at 330° C. instead of 290° C.

Reaction products were analyzed using GC/MS.

The following table shows the results from the reactor after 1 hour for both of the above runs. Though the dry furfural fed reactor (B) was at considerably higher temperature, and used twice the amount of catalyst, the furfural conversion was considerably lower (90% vs. nearly 100%). These results demonstrate the impact of water feed on the reaction.

TABLE 1

| Run | Water Added (wt %) | Temp (° C.) | Catalyst (g) | Furfural Conv(%) | Sel Furan (%) | Sel THF (%) | Sel Others (%) |
|---|---|---|---|---|---|---|---|
| A | 3 | 290 | 2.01 | 99.9% | 77.1% | 20.1% | 2.8% |
| B | 0 | 330 | 4.04 | 90.7% | 97.9% | 0.5% | 1.6% |

Example 2

Example 1 was repeated except that the reactor temperature was 270° C. instead of 290° C. and with 4 grams of catalyst instead of 2 grams. Data showing furfural conversion, selectivity for furan, and selectivity for tetrahydrofuran (THF) over several hours are presented in Table 2. Samples were drawn at the indicated times and analyzed using GC/MS. Markedly higher decarbonylation activity and better selectivity to furan were achieved using wet furfural (3 wt % added water).

TABLE 2

| Added water in furfural (wt %) | Time (hours) | Furfural Conversion (%) | Furan selectivity (%) | THF selectivity (%) |
|---|---|---|---|---|
| 3 | 1.0 | 97.0 | 92.3 | 2.9 |
| 3 | 2.0 | 97.2 | 92.4 | 2.8 |
| 3 | 5.0 | 94.1 | 93.9 | 1.8 |
| 0 | 1.8 | 69.3 | 88.6 | 3.7 |
| 0 | 2.8 | 71.8 | 90.3 | 2.6 |
| 0 | 5.3 | 63.2 | 90.8 | 1.7 |

It is to be appreciated that certain features of the invention which are, for clarity, described above and below in the context of separate embodiments, can also be provided in combination in a single embodiment. Conversely, various features of the invention that are, for brevity, described in the context of a single embodiment, can also be provided separately or in any subcombination. Further, reference to values stated in ranges includes each and every value within that range.

What is claimed is:

1. A process for the synthesis of a compound as represented by the following structure of Formula (I)

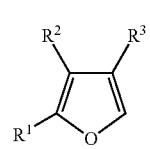

I by
(a) providing a vapor phase mixture of water and a compound as represented by the following structure of Formula (II),

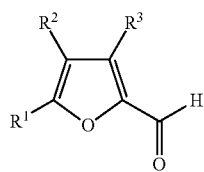

wherein the water is present at about 1 to about 30 wt % based on the weight of water plus Formula (II) compound;
(b) optionally, co-feeding the Formula (II) compound with hydrogen,
(c) heating a supported Pd catalyst, and
(d) contacting the vapor phase mixture and the catalyst to produce a Formula (I) product;
wherein $R^1$, $R^2$, and $R^3$ are each independently selected from H and a $C_1$ to $C_4$ hydrocarbyl group.

2. The process according to claim 1 wherein $R^1$, $R^2$, and $R^3$ are each H.

3. The process according to claim 1 wherein the Formula (II) compound is mixed with hydrogen in a ratio of between about 0.1 and about 5.0 moles of hydrogen per mole of Formula (II) compound.

4. The process according to claim 3 wherein the Formula (II) compound is mixed with hydrogen in a ratio of between about 0.5 and about 2.5 moles of hydrogen per mole of Formula (II) compound.

5. The process according to claim 1 wherein contacting the Formula (II) compound and the catalyst to produce a Formula (I) product occurs in the gas phase at a temperature that is in the range of from about 200° C. to about 400° C.

6. The process according to claim 5 wherein the temperature is in the range of from about 270° C. to about 330° C.

7. The process according to claim 1, further comprising purifying the Formula (I) product.

8. The process according to claim 1, wherein the Pd is supported on alumina.

9. The process according to claim 1, further comprising regenerating the catalyst by feeding a mixture of air and steam, with a composition of between about 2 volume % and about 40 volume % air, to the catalyst bed at a temperature between about 300° C. and about 500° C. for a time between about 10 seconds and about 100 hours.

10. The process according to claim 1 further comprising a step of subjecting the Formula (I) compound to a reaction to prepare therefrom tetrahydrofuran, polytetramethylene glycol, polyetherester elastomers, and polyurethane elastomers.

11. The process according to claim 1 further comprising a step of subjecting the Formula (I) compound to a hydrogenation reaction to convert into tetrahydrofuran.

12. The process according to claim 11 further comprising preparing polytetramethylene ether glycol from tetrahydrofuran.

13. The process according to claim 12 further comprising reacting polytetramethylene ether glycol with 1,4-butanediol and terephthalic acid to produce polyetherester elastomers.

14. The process according to claim 12 further comprising reacting polytetramethylene ether glycol with diisocyanates to produce polyurethanes.

* * * * *